United States Patent [19]

Ritz et al.

[11] Patent Number: 5,693,793
[45] Date of Patent: Dec. 2, 1997

[54] PREPARATION OF CAPROLACTAM FROM 6-AMINOCAPRONITRILE

[75] Inventors: Josef Ritz, Ludwigshafen; Eberhard Fuchs, Frankenthal; Guido Voit, Schriesheim; Günther Achhammer, Mannheim; Rolf Fischer, Heidelberg, all of Germany

[73] Assignee: BASF Aktiengesellschaft, Ludwigshafen, Germany

[21] Appl. No.: 707,476

[22] Filed: Sep. 5, 1996

[30] Foreign Application Priority Data

Jul. 17, 1996 [DE] Germany ............... 196 28 805.3

[51] Int. Cl.$^6$ ............................................. C07D 201/08
[52] U.S. Cl. ....................................................... 540/539
[58] Field of Search ............................................. 540/539

[56] References Cited

U.S. PATENT DOCUMENTS 5,496,941  3/1996  Ritz et al. .............................. 540/539

Primary Examiner—Robert T. Bond
Attorney, Agent, or Firm—Keil & Weinkauf

[57] ABSTRACT

A process for preparing caprolactam by cyclization of 6-aminocapronitrile in the presence of water at elevated temperature and in the presence or absence of a catalyst and a solvent, comprises a) removing from the cyclization reaction effluent ("reaction effluent I") caprolactam and all components boiling higher than caprolactam ("high boilers"), b) treating the high boilers of stage a) with phosphoric acid and/or polyphosphoric acid at from 200 to 350° C. to obtain a reaction effluent II, and c) removing caprolactam formed and any 6-aminocapronitrile from reaction effluent II of stage b) to obtain separation from unconverted high boilers and acid used.

5 Claims, No Drawings

PREPARATION OF CAPROLACTAM FROM 6-AMINOCAPRONITRILE

The present invention relates to an improved process for preparing caprolactam by cyclization of 6-aminocapronitrile in the presence of water at elevated temperature and in the presence or absence of a catalyst and a solvent.

It is known to react 6-aminocapronitrile with water to form caprolactam and ammonia. This can be done both in the gas phase and in the liquid phase. For instance, high caprolactam yields are obtained in U.S. Pat. Nos. 4,628,085 and 4,625,023 in the gas phase in the presence of metal oxides such as alumina and silica or in EP-A 659,741 in the presence of metal phosphates. According to U.S. Pat. No. 2,301,964, it is possible to prepare caprolactam in high yield in the liquid phase even without a catalyst. The cyclization in the liquid phase in the presence of catalysts such as homogeneously dissolved metal salts is described in FR-A 2,029,540. DE-A 4,339,648 and DE-A 4,422,610 describe the liquid-phase reaction in the presence of suspended or fixed-bed metal oxides.

However 6-aminocapronitrile is cyclized to caprolactam, the desired product of value, caprolactam, is customarily obtained together with byproducts which have boiling points higher than the boiling point of caprolactam. The amount of these high boilers can vary appreciably depending on the cyclization catalyst used, if any, and the conditions of the cyclization.

The main constituents of these high boilers are dimers and oligomers of varying molecular weight. The composition of these high boilers differs from the composition of the polymers obtained in the polymerization of caprolactam.

The cyclization of 6-aminocapronitrile with water to form caprolactam and ammonia gives rise to high boilers of the formula I

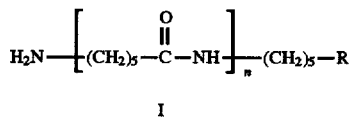

I where R is carboxyl, carbamoyl, nitrile or, when alcohols are used as solvents in the cyclization of 6-aminocapronitrile, an ester group n is an integer from 2 to about 50, but the average value of n over all compounds I is generally less than 5.

By contrast, the ring-opening polycondensation of caprolactam in the presence of water gives rise to polymers (nylon 6) of the formula II:

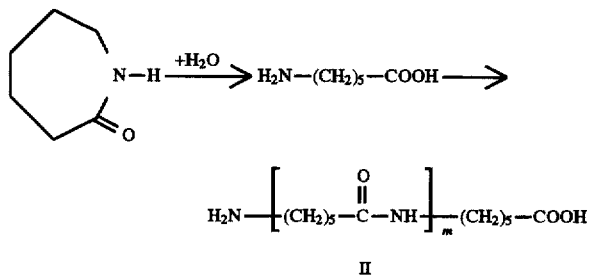

II

In contradistinction to the high boilers of the formula I, m is much more than 1000 in the polymers of the formula II and R is only carboxyl.

It follows that the high boilers mixtures of the formula I differ in their chemical structure and their molecular weights significantly from nylon 6 which is obtained from caprolactam.

It is known to depolymerize nylon 6 or nylon-6-including product mixtures back to caprolactam. The caprolactam used for the synthesis of nylon 6 has hitherto almost without exception been prepared by Beckmann rearrangement of cyclohexanoneoxime. The depolymerization of nylon 6 or nylon-6-including product mixtures is customarily effected using acidic or basic catalysts at elevated temperature, frequently under the action of steam.

Chem. Ing. Techn. 45 (1973), 1510, describes an industrial depolymerization process using superheated steam. The workup necessitates concentrating a caprolactam-water solution.

According to the process of EP-A 209 021, the depolymerization to caprolactam is carried out in a fluidized bed of alumina. EP-A 529 470 teaches the addition of potassium carbonate as a catalyst to a nylon 6 depolymerization which is carried out at from 250° to 320° C. with simultaneous distillative removal of the caprolactam under reduced pressure.

DE-A 2,440,243 describes the depolymerization to caprolactam of nylon-including textile wastes using acid mixtures comprising water and phosphoric acid, such as phosphoric acid and phosphorous acid, phosphoric acid, phosphorous acid and boric acid, phosphoric acid and hydrochloric acid (Examples 1 to 3).

DE-A 2,164,462 describes a process for preparing ε-aminocaproic acid and cyclic dimeric caprolactam from oligomers of caprolactam by treating the oligomers with sulfuric acid at above 50° C., diluting with water, removing the precipitated cyclic dimeric caprolactam, treating the filtrate with a weakly basic ion exchanger, concentrating, and isolating the ε-aminocaproic acid crystals.

U.S. Pat. No. 3,182,055 describes a continuous process for preparing caprolactam by treating polycaprolactam with from 0.1 to 5 parts of phosphoric acid per 100 parts of the polymer and steam at temperatures within the range from 220° to 375° C. and a pressure within the range from 0.5 to 6 bar, the resulting caprolactam being removed from the system with the steam.

WO 94/06763 discloses a continuous process for recovering caprolactam from carpets comprising nylon 6. The comminuted material comprising nylon 6 is depolymerized by passing superheated steam into it in the presence of phosphoric acid. Examples 1, 3, 4 and 5 reveal that 40% by weight, 8% by weight, 24% by weight and 60% by weight, respectively, of phosphoric acid are required, based on the nylon 6 content of the material. The corresponding caprolactam crude yields are respectively 56%, 37%, 89% and 80%, again based on the nylon 6 content of the material.

Existing processes, especially the continuous ones, for depolymerizing nylon 6 or nylon-6-including material back to caprolactam have serious disadvantages. First, relatively large amounts of steam are required for separating off the caprolactam. The resulting water has to be removed again later from the caprolactam, which is very costly in terms of energy. And secondly, phosphoric acid and the unutilizable high boiler fractions give rise to distillation residues which have to be disposed of. In most cases landfilling is the only disposal option.

It is clear from the cited references that a high caprolactam yield depolymerization of nylon 6 polymer requires widely varying amounts of steam and phosphoric acid depending on the composition of the polymer material.

R is carbamoyl or nitrile in the compounds of the formula I. It is known that carbamoyl and nitrile groups form ammonia in the presence of acids and water (see H. Beyer, Lehrbuch der organis-chen Chemie, Verlag S. Hirzel, Leipzig, 20th Edition, p. 252).

When an attempt is made to break down compounds I to caprolactam by treating them in the presence of a small amount of acid, it is therefore likely that the ammonia formed will neutralize at least some of the acid which has been added, so that either more acid has to be added or the attempted deoligomerization will not go to completion.

It is an object of the present invention to develop a process whereby the high boilers formed in the cyclization of 6-amino-capronitrile can be converted into very pure caprolactam in a very high yield using very little energy and acid. The process shall further ideally completely obviate disposal by landfilling.

We have found that this object is achieved by an improved process for preparing caprolactam by cyclization of 6-aminocapronitrile in the presence of water at elevated temperature and in the presence or absence of a catalyst and a solvent, which comprises a) removing from the cyclization reaction effluent ("reaction effluent I") caprolactam and all components boiling higher than caprolactam ("high boilers"), b) treating the high boilers of stage a) with phosphoric acid and/or polyphosphoric acid at from 200° to 350° C. to obtain a reaction effluent II, and c) removing caprolactam formed and any 6-aminocapronitrile from reaction effluent II of stage b) to obtain separation from unconverted high boilers and acid used.

In this invention, the starting caprolactam is prepared from 6-aminocapronitrile. This cyclization of 6-aminocapronitrile can be carried out in the liquid or gas phase according to known methods, for example according to a process as described in U.S. Pat. Nos. 2,301,964, 2,357,484, EP-A 150 295 or DE-A 43 19 134 by reacting 6-aminocapronitrile with water in the liquid phase in a conventional manner to form caprolactam and ammonia.

When no catalyst is used, the reaction is generally carried out at a temperature within the range from 200° to 375° C. using reaction times within the range from 10 to 90, preferably from 10 to 30, min. The solvent used is generally water, in which case the 6-aminocapronitrile content, based on the water, is generally below 30, preferably within the range from 10 to 25, % by weight.

When the reaction is carried out in the liquid phase in the presence of a catalyst, it is customary to use a temperature within the range from 50° to 330° C., a water quantity within the range from 1.3 to 50, preferably from 1.3 to 30, mol per mole of 6-aminocapronitrile, and a reaction time within the range from 10 min to several hours. When an organic solvent is used, especially an alcohol, it is customary to use a water quantity within the range from 1.3 to 5 mol per mole of 6-aminocapronitrile.

It is customary for the cyclization reaction effluent first to be worked up by distillation to remove ammonia, water and any organic solvent. The catalyst, if any, present in the bottom product is generally separated from the caprolactam by one of the customary methods and recycled into the cyclization reactor. The crude caprolactam is generally converted by a conventional purifying operation such as distillation into pure lactam, which is then available for polymerization to form polycaprolactam.

In a preferred embodiment, 6-aminocapronitrile is reacted with water in the liquid phase using heterogeneous catalysts.

The reaction is carried out in the liquid phase at temperatures from generally 140° to 320° C., preferably from 160° to 280° C.; the pressure is generally within the range from 100 kPa to 25 MPa, preferably from 500 kPa to 15 MPa, and care has to be taken to ensure that the reaction mixture is predominantly liquid under the conditions employed. The residence times generally range from 1 to 120, preferably from 1 to 90, especially from 1 to 60 min. In some cases residence times from 1 to 10 min have proven completely sufficient.

The amount of water used per mole of 6-aminocapronitrile is generally at least 0.01 mol, preferably from 0.1 to 20 mol, especially from 1 to 5 mol.

The 6-aminocapronitrile is advantageously used in the form of a from 1 to 50% strength by weight, especially from 5 to 50% strength by weight, particularly preferably from 5 to 30% strength by weight solution in water (in which case the solvent is also the coreactant) or in water-solvent mixtures. Examples of suitable solvents are alkanols such as methanol, ethanol, n- and i-propanol, n-, sec-, i- and t-butanol and polyols such as diethylene glycol and tetraethylene glycol, hydrocarbons such as petroleum ether, benzene, toluene, xylene, lactams such as pyrrolidone or caprolactam or alkyl-substituted lactams such as N-methylpyrrolidone, N-methylcaprolactam or N-ethylcaprolactam and also carboxylic esters, preferably of carboxylic acids having from 1 to 8 carbon atoms. Ammonia can also be present in the reaction. It is also possible to use mixtures of organic solvents, of course. Mixtures of water and alkanols in a water/alkanol weight ratio of from 1 to 75/25 to 99, preferably from 1 to 50/50 to 99, have been found to be particularly advantageous in some cases.

It is similarly possible in principle to use the 6-aminocapronitrile as solvent as well as reactant.

Examples of heterogeneous catalysts which can be used include acidic, basic or amphoteric oxides of some elements of the second, third or fourth main group of the Periodic Table, such as calcium oxide, magnesium oxide, boron oxide, aluminum oxide, tin oxide or silicon dioxide as pyrogenic silica, as silica gel, diatomaceous earth, quartz or mixtures thereof, also oxides of metals of the second to sixth subgroup of the Periodic Table such as titanium dioxide, amorphous, as anatase and/or rutile, zirconium dioxide, zinc oxide, manganese oxide or mixtures thereof. It is also possible to use oxides of the lanthanides and actinides, such as cerium oxide, thorium oxide, praseodymium oxide, samarium oxide, rare earth mixed oxide or mixtures thereof with the aforementioned oxides. Examples of further catalysts which can be used are:

vanadium oxide, niobium oxide, iron oxide, chromium oxide, molybdenum oxide, tungsten oxide or mixtures thereof. Mixtures between the oxides mentioned are likewise possible. Some sulfides, selenides and tellurides such as zinc telluride, tin selenide, molybdenum sulfide, tungsten sulfide, sulfides of nickel, zinc and chromium are also usable.

The aforementioned compounds can be doped with or include compounds of the 1st and 7th main groups of the Periodic Table.

Suitable catalysts further include zeolites, phosphates and heteropolyacids and also acidic and alkaline ion exchangers, for example Naphion®.

If desired, these catalysts may include up to 50% by weight each of copper, tin, zinc, manganese, iron, cobalt, nickel, ruthenium, palladium, platinum, silver or rhodium.

Depending on their composition, the catalysts can be used with or without a support. For instance, titanium dioxide can be used as a titanium dioxide extrudate or as titanium dioxide applied in a thin layer to a support. To apply titanium dioxide to a support such as silicon dioxide, aluminum dioxide or zirconium dioxide it is possible to use any method described in the literature. For instance, a thin titanium dioxide layer can be applied by hydrolysis of organotitanium compounds such as titanium isopropoxide or titanium butoxide or by hydrolysis of $TiCl_4$ or other inorganic titanium compounds. It is also possible to use titanium dioxide sols.

Other suitable compounds are zirconyl chloride, aluminum nitrate and cerium nitrate.

Suitable supports are powders, extrudates or tablets of the aforementioned oxides themselves or other stable oxides such as silicon dioxide. The supports used can be made macroporous to improve the mass transport.

In a further preferred embodiment, 6-aminocapronitrile is cyclized in the liquid phase with water at elevated temperature without catalyst by heating an aqueous solution of 6-aminocapronitrile in the liquid phase without addition of a catalyst in a reactor to obtain a mixture I consisting essentially of water, caprolactam and a high-boiling fraction ("high boilers"). In this preferred embodiment, water is preferably used in excess, particularly preferably in an amount of from 10 to 150, especially from 20 to 100, mol of water per mole of 6-aminocapronitrile, to obtain an aqueous solution of 6-aminocapronitrile.

In a further preferred embodiment, it is customary to use from 5 to 25 mol of water per mole of 6-aminocapronitrile, in which case the solution can generally be further diluted to 5–25% by weight of 6-aminocapronitrile by addition of an organic solvent.

Examples of suitable solvents include:

$C_1$–$C_4$-alkanols such as methanol, ethanol, n-, i-propanol, butanols such as n-butanol, isobutanol, tert-butanol and sec-butanol, glycols such as ethylene glycol, diethylene glycol, triethylene glycol, tetraethylene glycol, ethers such as methyl tert-butyl ether, diethylene glycol diethyl ether, $C_6$–$C_{10}$-alkanes such as n-hexane, n-heptane, n-octane, n-nonane, n-decane and also cyclohexane, benzene, toluene, xylene, lactams such as pyrrolidone, caprolactam or N-$C_1$–C4-alkyl-lactams such as N-methylpyrrolidone, N-methylcaprolactam or N-ethylcaprolactam.

In a further embodiment, from 0 to 5, preferably from 0.1 to 2, % by weight of ammonia, hydrogen or nitrogen can be added to the reaction mixture.

The reaction is preferably carried out at a temperature within the range from 200° to 370° C., preferably from 220° to 350° C., particularly preferably from 240° to 320° C.

The reaction is customarily carried out under superatmospheric pressure, the pressure generally being chosen within the range from 0.1 to 50, preferably from 5 to 25, MPa in such a way that the reaction mixture is preferably in the liquid phase.

The reaction time depends essentially on the chosen process parameters and is generally within the range from 10 to 180, preferably from 20 to 90, min in the case of the continuous process. In the case of shorter reaction times, the yield generally decreases, while longer reaction times generally lead to the formation of troublesome oligomers.

The cyclization is preferably carried out continuously, preferably in a tubular reactor, in stirred kettles or a combination thereof.

The cyclization can also be carried out batchwise. In this case the reaction time is customarily within the range from 30 to 180 min.

The effluent is generally a mixture consisting essentially of from 50 to 98, preferably from 80 to 95%, by weight of water and solvent and from 2 to 50, preferably from 5 to 20, % by weight of a mixture consisting essentially of from 0 to 10% by weight of low-boiling fractions, especially aminocapronitrile and the corresponding aminocaproic ester, based on the caprolactam-including mixture, of from 50 to 95, preferably from 65 to 90%, by weight of caprolactam and of from 5 to 50, preferably from 10 to 35%, by weight of a high-boiling fraction ("high boilers").

The process of this invention comprises removing, in stage a), from the cyclization reaction effluent (reaction effluent I) caprolactam and also a further fraction having a higher boiling point than caprolactam ("high boilers") by distillation, preferably by fractional distillation.

In a preferred embodiment, the distillative removal of caprolactam and the high boilers is preceded by the removal of ammonia and, if desired, water and any solvent present and/or unconverted 6-aminocapronitrile by conventional methods as described for exi ample in U.S. Pat. No. 2,301, 964, DE-A 4,339,648, DE-A 4,422,610, EP-A 659,741, U.S. Pat. No. 4,628,085 or U.S. Pat. No. 6,625,023. In a further preferred embodiment, water, solvent if present and 6-aminocapronitrile are recycled back into the cyclization stage. Ammonia is generally removed from the system.

The high boilers introduced into the high boilers deoligomerization treatment of stage b) can further comprise monomeric caprolactam, for example from 0.1 to 50% by weight, especially from 10 to 40% by weight, based on the higher boilers mixture.

The high boilers are treated according to this invention with phosphoric acid and/or polyphosphoric acid. The phosphoric acid used can be water-free or aqueous phosphoric acid. Preference is given to using commercial 85% strength by weight aqueous phosphoric acid.

The amount of acid (calculated as 100% acid in the case of phosphoric acid) is customarily from 0.01 to 10% by weight, preferably from 0.02 to 2% by weight, particularly preferably from 0.03 to 0.1% by weight, based on the high boilers used.

The high boilers treatment of this invention is carried out at from 180° C. to 350° C., preferably from 200° C. to 330° C., particularly preferably from 220° C. to 320° C.

The high boilers treatment is customarily carried out at a pressure within the range from 10 kPa to i MPa, preferably from 50 kPa to 500 kPa, particularly preferably from 80 kPa to 200 kPa.

In a preferred embodiment, the high boilers are broken down to caprolactam using 85% strength by weight phosphoric acid (0.075% by weight of water, based on the high boilers mixture) without additional steam.

In a further preferred embodiment, superheated steam is passed into the high boilers mixture and the monomeric caprolactam formed is separated by distillation together with steam from phosphoric acid and remaining high boilers.

The temperature of the superheated steam is generally within the range from 180° to 400° C., in particular from 200° to 350° C. The amount of water introduced in the form of steam is customarily from 0.05 g to 20 g of water, preferably from 0.1 g to 10 g, particularly preferably from 0.5 g to 5 g, per g of high boilers mixture.

The residence times are chosen as a function of temperature, pressure, acid and water quantity, customarily within the range from 0.1 to 7 hours, preferably within the range from 1 to 5 hours.

Furthermore, the treatment of the high boilers with an acid, especially phosphoric acid and polyphosphoric acid, can be carried out batchwise or continuously.

The caprolactam resulting from the breakdown of the high boilers mixtures, which is obtained as an aqueous solution, can still include small amounts of 6-aminocapronitrile.

A batchwise process can be carried out for example by heating a mixture of high boilers in acid, especially phosphoric acid, to the desired reaction temperature, introducing superheated steam, and distilling the resulting caprolactam and any 6-aminocapronitrile and water through a column placed on the reactor and obtaining a bottom product comprising a mixture of unconverted high boilers and acid used. The bottom product can be repeatedly reused, in a preferred embodiment. For this, it is freshly admixed with high boilers and again subjected to the treatment with steam.

A continuous process generally comprises feeding high boilers, phosphoric acid and/or polyphosphoric acid and superheated steam into a reactor. The reaction mixture can be separated after the residence time into caprolactam and any 6-aminocapronitrile and water as overhead product and a mixture of high boilers and phosphoric acid/polyphosphoric acid as bottom product. This bottom product can preferably be recycled.

According to this invention, the caprolactam formed in stage b) and any 6-aminocapronitrile are removed from the reaction effluent of stage b) (reaction effluent II) to obtain separation from unconverted high boilers and acid used; the removed caprolactam may still include water and, if desired, 6-aminocapronitrile, according to the desired degree of separation.

The caprolactam removed in stage c) can be subjected to further purification steps in a conventional manner.

In a preferred embodiment, the caprolactam obtained in stage c) is introduced into the workup stage of the crude caprolactam obtained in the cyclization of 6-aminocapronitrile with water and/or combined with the caprolactam obtained in stage a).

The preparation of on-spec pure caprolactam from the crude caprolactam obtained in the cyclization of 6-aminocapronitrile and the added, regenerated caprolactam can be effected for example according to the process described in U.S. Pat. No. 5,496,941, which discloses a reaction sequence of catalytic hydrogenation, acidic and alkaline distillation to obtain a pure caprolactam which meets the specification in respect of the parameters typical of Beckmann caprolactam, such as permanganate titration number (PTN), permanganate absorption number (PAN), UV number, free and volatile bases.

It is surprising that the high boilers mixtures of the formula I can be used to obtain caprolactam and 6-aminocapronitrile with yields of above 90%. Since the number of 6-aminocaproic acid units in the high boilers is below 5 on average, the different terminal members (R=—CO—NH$_2$; —CN, —COOR) must have been highly involved in caprolactam formation, too. That this should be possible under the conditions of the phosphoric acid treatment was unforeseeable.

It is also surprising that higher caprolactam yields than in the prior art should be obtainable with very low phosphoric acid and/or polyphosphoric acid quantities and relatively small water quantities.

Nor was it forseeable, finally, that the pure lactam obtained from mixtures of cyclization and regeneration lactam following purification (hydrogenation, acidic distillation, alkaline distillation) would meet the desired specification requirements.

EXAMPLES

Example 1

Caprolactam by Cyclization of 6-aminocapronitrile

In a 20 ml capacity tubular reactor (diameter 6 mm, length 710 mm) packed with titanium dioxide (anatase) in the form of 1.5 mm extrudates and heated to 225° C., 70 g/h of a solution of 10% by weight of 6-aminocapronitrile, 3.2% by weight of water and ethanol (remainder) were reacted at 100 bar.

Quantitative gas chromatography of the reaction effluent revealed the following yields: 90% of caprolactam, 4% of ethyl 6-aminocaproate and also 2% of 6-aminocapronitrile.

A product stream collected over 350 hours was freed of ammonia, ethanol and water, and the resulting crude lactam was distilled to obtain 102 g of low boilers and 226 g of high boilers with a boiling point of higher than 190° C. at a pressure of 1 mbar as well as 2140 g of caprolactam. The low boilers were essentially ethyl 6-aminocaproate and unconverted 6-aminocapronitrile, the high boilers were essentially oligomers.

In the examples which follow, the high boilers prepared by this example for the deoligomerization runs additionally included monomeric caprolactam, in part.

Example 2

Caprolactam by Deoligomerization of High Boilers Using Phosphoric Acid (Without Steam)

In a 500 ml three-necked flask with fitted column, a mixture of 250 g of the high boilers prepared in Example 1 and freed of residual caprolactam in a further distillation, and 1.25 g of 85% strength by weight phosphoric acid was heated. 166 g of a product mixture distilled over at 250°–270° C./1013 mbar (base of column temperature 350° C.), which were found by gas chromatography to include 151 g of caprolactam (60%, based on high boilers used).

Example 3

Caprolactam by Deoligomerization of High Boilers Using Phosphoric Acid (With Steam)

In a 500 ml three-necked flask with fitted column, a mixture of 250 g of the high boilers prepared according to Example 1 (monomeric caprolactam content: 36%) and 1.25 g of 85% strength by weight phosphoric acid was heated to 350° C. At that temperature and atmospheric pressure 500 g/h of superheated steam at 350° C. were introduced over a period of 70 minutes. The overhead product was, after condensation, 724 g of an aqueous solution which according to gas chromatography comprised 30.2% of caprolactam and 0.6% of 6-aminocapronitrile. 10 g of a mixture of high boilers and catalyst remained behind in the reaction flask.

This example shows that the high boilers used can be converted into caprolactam to 80% (based on high boilers used). It also makes clear that only 6% of high boilers+phosphoric acid (based on high boilers used) has to be disposed of.

Example 4

Caprolactam by Deoligomerization of High Boilers Using Polyphosphoric Acid (With Steam)

In a 500 ml three-necked flask with fitted column, a mixture of 250 g of the high boiler prepared according to Example 1 (monomeric caprolactam content: 36%) and 1.25 g of commercially available polyphosphoric acid (density= 2.8 g/ml) was heated to 250° C. At that temperature and atmospheric pressure 250 g/h of superheated steam at 300° C. were introduced over a period of 3 hours. The overhead product was, after condensation, 1075 g of an aqueous solution which according to gas chromatography comprised 21.8% of caprolactam and 0.2% of 6-aminocapronitrile. 6 g of a high boilers/catalyst mixture remained behind in the reaction flask.

The experiment shows that the high boilers used can be converted into caprolactam to 90%. It also makes clear that only 4% of high boilers (based on the high boilers quantity used) has to be disposed of.

Example 5

The 6 g of residue obtained in Example 4 following the high boilers deoligomerization with polyphosphoric acid was again admixed with 250 g of a high boilers mixture. (monomeric caprolactam content 90 g). The caprolactam recovery was carried out as described in Example 4. The caprolactam yield minus monomeric caprolactam already present was 89%. 11 g of high boilers remained behind in the reaction flask.

We claim:

1. A process for preparing caprolactam by cyclization of 6-aminocapronitrile in the presence of water at elevated temperature and in the presence or absence of a catalyst and a solvent, which comprises
    a) removing from the cyclization reaction effluent ("reaction effluent I") caprolactam and all components boiling higher than caprolactam ("high boilers"),
    b) treating the high boilers of stage a) with phosphoric acid and/or polyphosphoric acid at from 200° to 350° C. to obtain a reaction effluent II, and
    c) removing caprolactam formed and any 6-aminocapronitrile from reaction effluent II of stage b) to obtain separation from unconverted high boilers and acid used.

2. A process as claimed in claim 1, wherein the treatment with phosphoric acid and/or polyphosphoric acid in stage b) is carried out with from 0.01 to 10% by weight of phosphoric acid and/or polyphosphoric acid, based on the high boilers used.

3. A process as claimed in claim 1, wherein from 0.05 g to 20 g of water per g of high boilers is introduced into the reaction mixture of stage b) in the form of superheated steam.

4. A process as claimed in any of claims 1, wherein ammonia and, if desired, water, and also any .solvent present are removed by distillation before the distillation of caprolactam and high boilers in stage a).

5. A process as claimed in any of claims 1, wherein the caprolactam removed in stage c) is, if necessary after removal of 6-aminocapronitrile, combined with the caprolactam of stage a) and, if desired, the combined caprolactam is worked up in a conventional manner to on-spec caprolactam.

* * * * *